(12) United States Patent
Leggett et al.

(10) Patent No.: US 11,642,028 B2
(45) Date of Patent: May 9, 2023

(54) FORCE READING DEVICES AND METHODS

(71) Applicant: Aegle BioTech, LLC, Atlanta, GA (US)

(72) Inventors: Tanner Jackson Leggett, Atlanta, GA (US); Richard David Lehner, Atlanta, GA (US); Daniel Joseph Kuntz, Atlanta, GA (US); Jorge David Guigou, Atlanta, GA (US)

(73) Assignee: Aegle BioTech, LLC, Atlanta, GA (US)

( * ) Notice: Subject to any disclaimer, the term of this patent is extended or adjusted under 35 U.S.C. 154(b) by 152 days.

(21) Appl. No.: 16/892,429

(22) Filed: Jun. 4, 2020

(65) Prior Publication Data

US 2020/0383575 A1 Dec. 10, 2020

Related U.S. Application Data (60) Provisional application No. 62/857,306, filed on Jun. 5, 2019.

(51) Int. Cl.
*A61B 5/00* (2006.01)
*G01L 5/00* (2006.01)
*G01L 1/26* (2006.01)

(52) U.S. Cl.
CPC .......... *A61B 5/0053* (2013.01); *A61B 5/6843* (2013.01); *G01L 1/26* (2013.01); *G01L 5/0038* (2013.01); *A61B 2562/0247* (2013.01)

(58) Field of Classification Search
CPC ....... G01L 1/26; G01L 5/0038; A61B 5/0053; A61B 5/6843; A61B 2562/0247
See application file for complete search history.

(56) References Cited

U.S. PATENT DOCUMENTS

| | | | | |
|---|---|---|---|---|
| 4,024,372 A | * | 5/1977 | Herrmann | G01L 1/2243 219/121.14 |
| 8,161,823 B2 | * | 4/2012 | Berris, Jr. | G01B 7/22 73/780 |
| 2014/0207263 A1 | * | 7/2014 | Patzwald | G16H 50/30 700/91 |

FOREIGN PATENT DOCUMENTS

| | | | | |
|---|---|---|---|---|
| CN | 103647021 | * | 3/2014 | |
| CN | 106664668 A | * | 5/2017 | H04W 4/80 |
| CN | 113324683 A | * | 8/2021 | |
| JP | H07209066 A | * | 8/1995 | |
| JP | 2014207957 A | * | 11/2014 | A63B 23/04 |

* cited by examiner

*Primary Examiner* — Octavia Davis Hollington
(74) *Attorney, Agent, or Firm* — Perilla Knox & Hildebrandt LLP; Kenneth A. Knox (57) ABSTRACT

The present disclosure relates to force reading device. The products are multi-sensor, meaning they operate using two or more independent sensors, and communicate weight distribution and force data to the user in real time. The weight-lifter/user is notified by a visual aid via mobile app display and/or LCD screen and verbal feedback. Through real-time data feedback, the user is able to correct their form/balance as needed, in efforts to center their body weight and/or more evenly distribute their limbs. This in turn allows for the collection of data on how one may perform exercises and job tasks, and also offers a real-time solution for preventing injury and increasing exercise/job task functionality.

14 Claims, 14 Drawing Sheets

FORCE READING DEVICES AND METHODS

CROSS-REFERENCE TO RELATED APPLICATION

This application claims the benefit of and priority to U.S. Provisional Patent Application No. 62/857,306 entitled "FORCE READING DEVICES AND METHODS," filed on Jun. 5, 2019, the contents of which being incorporated by reference in its entirety herein.

BACKGROUND

There is currently no solution for fitness and health enthusiasts to measure exertion of force from each leg and/or arm in real-time, for example, while performing leg and/or arm lifting exercises, such as squats, leg presses, deadlifts, bench presses, chest presses, etc. Today, when performing high intensity leg/arm exercises that require force by pushing or pulling, the exerciser must use a best guess to assume the force is equal between the two legs and/or arms required for pushing or pulling the weight. More often than not, there is a favored leg or arm that exerts more force than the other, resulting in a plethora of health and fitness issues, such as back pain and inflammation, among others. These issues can lead to long term health issues that can ultimately affect the way one is able to live actively at an older age.

BRIEF SUMMARY OF THE INVENTION

Various embodiments for a force reading device are described, where the force reading device may include force reading shoe soles, force reading mats, force reading boards, force reading gloves, force reading moldable "strips" (e.g., moldable plastics), and associated devices that can be integrated into equipment and/or machinery, such as weight-lifting machinery.

A force reading device may include multiple sensors (e.g., two or more independent sensor data fields) that are able to communicate weight distribution and force information between users' limbs and body positioning in real-time to an end user, for instance, as they are performing the exercise and/or job task. The weight-lifter/user is notified by a visual aid via a mobile application and/or a display device as well as using verbal feedback.

Through real-time data feedback providing via the mobile application, a user is able to correct their form and/or balance as needed in an attempt to center their body weight, more evenly distribute their limbs, or apply forces more uniformly among multiple limbs. This in turn allows for the collection of data on how one may perform exercises and job tasks, and also offers a real-time solution for preventing injury, and increasing exercise and/or job task functionality.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Various embodiments for a force reading device are described, where the force reading device may include force reading shoe soles, force reading mats, force reading boards, force reading gloves, force reading moldable "strips" (e.g., moldable plastics), and associated devices that can be integrated into equipment and/or machinery, such as weight-lifting machinery.

A force reading device may include multiple sensors (e.g., two or more independent sensor data fields) that are able to communicate weight distribution and force information between users' limbs and body positioning in real-time to an end user, for instance, as they are performing the exercise and/or job task. The weight-lifter/user is notified by a visual aid via a mobile application and/or a display device as well as using verbal feedback.

Through real-time data feedback providing via the mobile application, a user is able to correct their form and/or balance as needed in an attempt to center their body weight, more evenly distribute their limbs, or apply forces more uniformly among multiple limbs. This in turn allows for the collection of data on how one may perform exercises and job tasks, and also offers a real-time solution for preventing injury, and increasing exercise and/or job task functionality.

Figure 1:
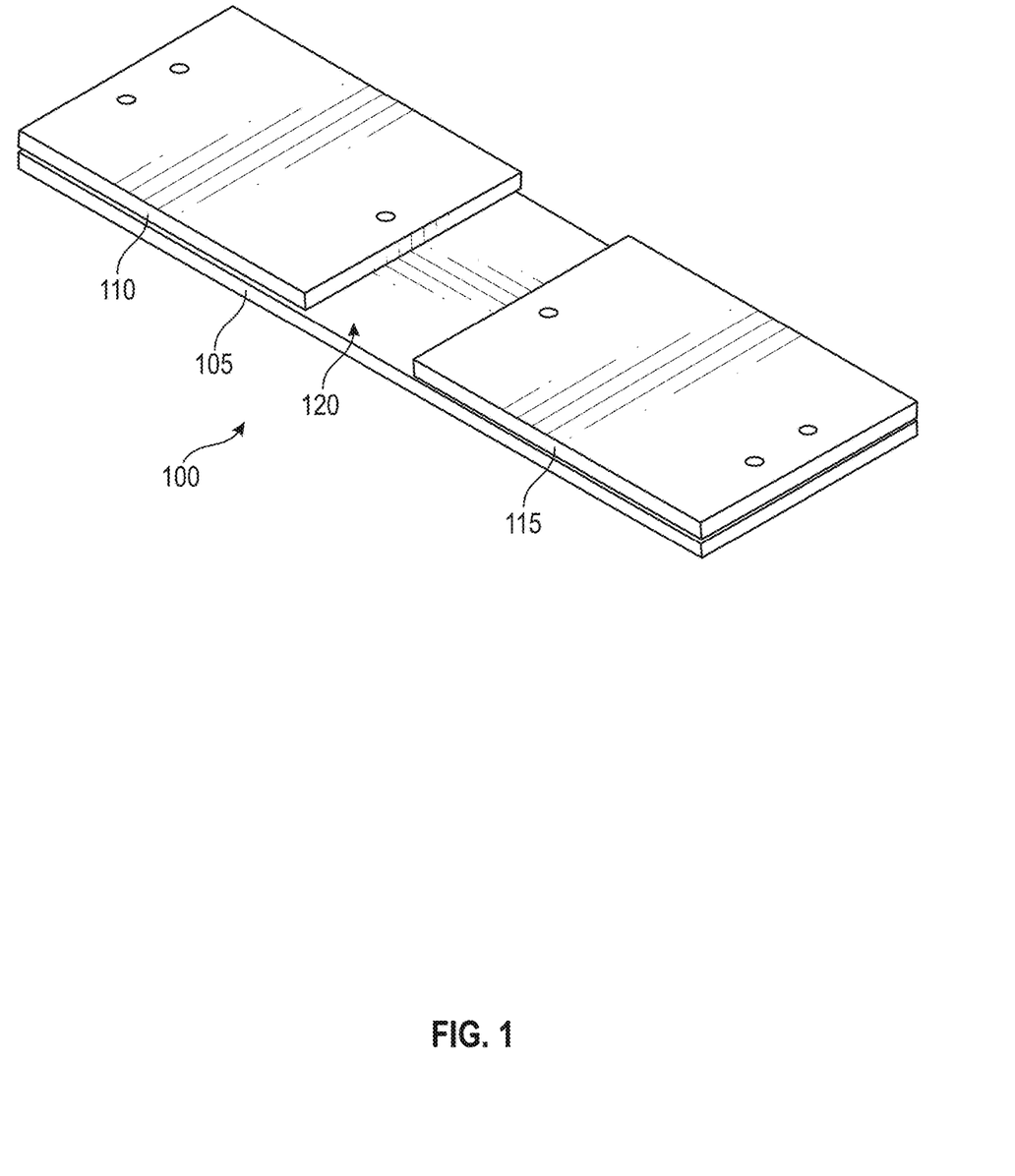
FIG. 1 is an isometric view of an embodiment of a force reading device according to various embodiments of the present disclosure.
Figure 2:
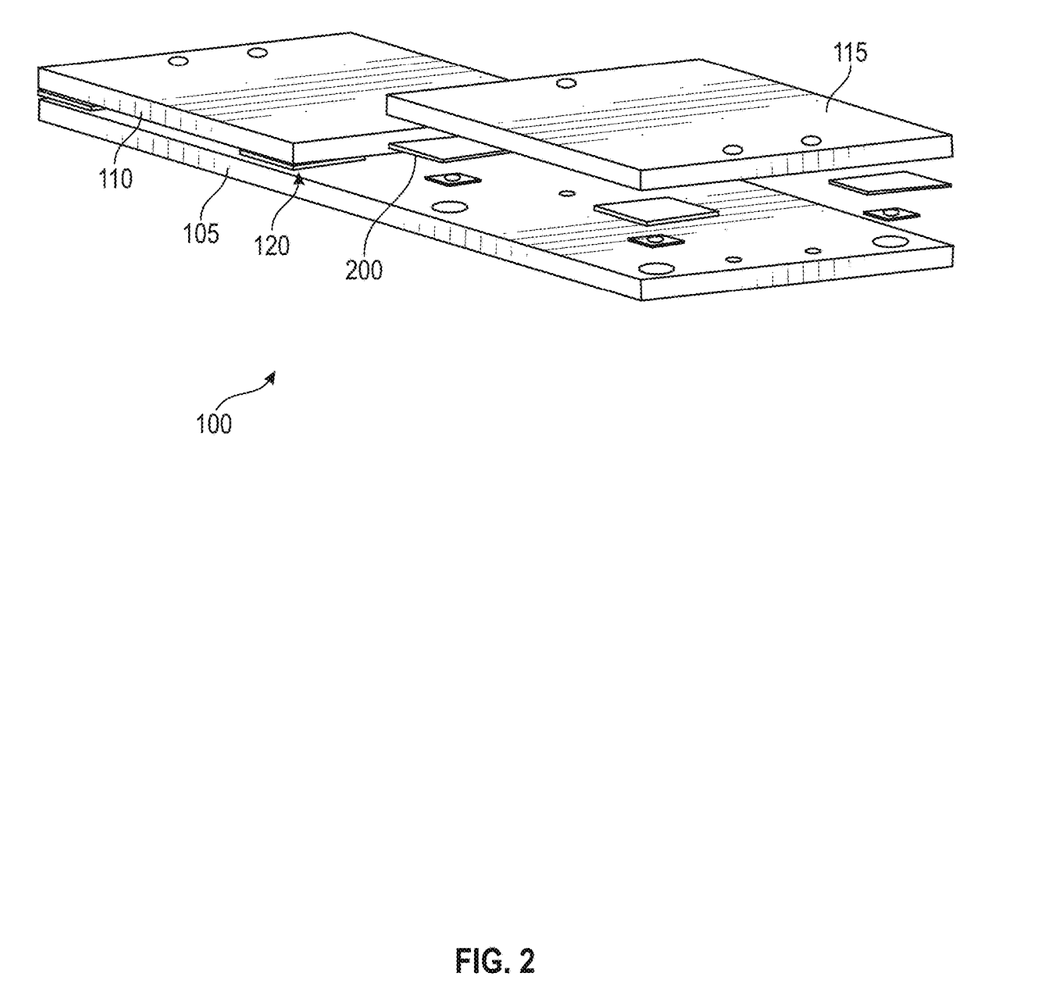
FIG. 2 is an exploded view of an embodiment of the force reading device according to various embodiments of the present disclosure.
Figure 3:
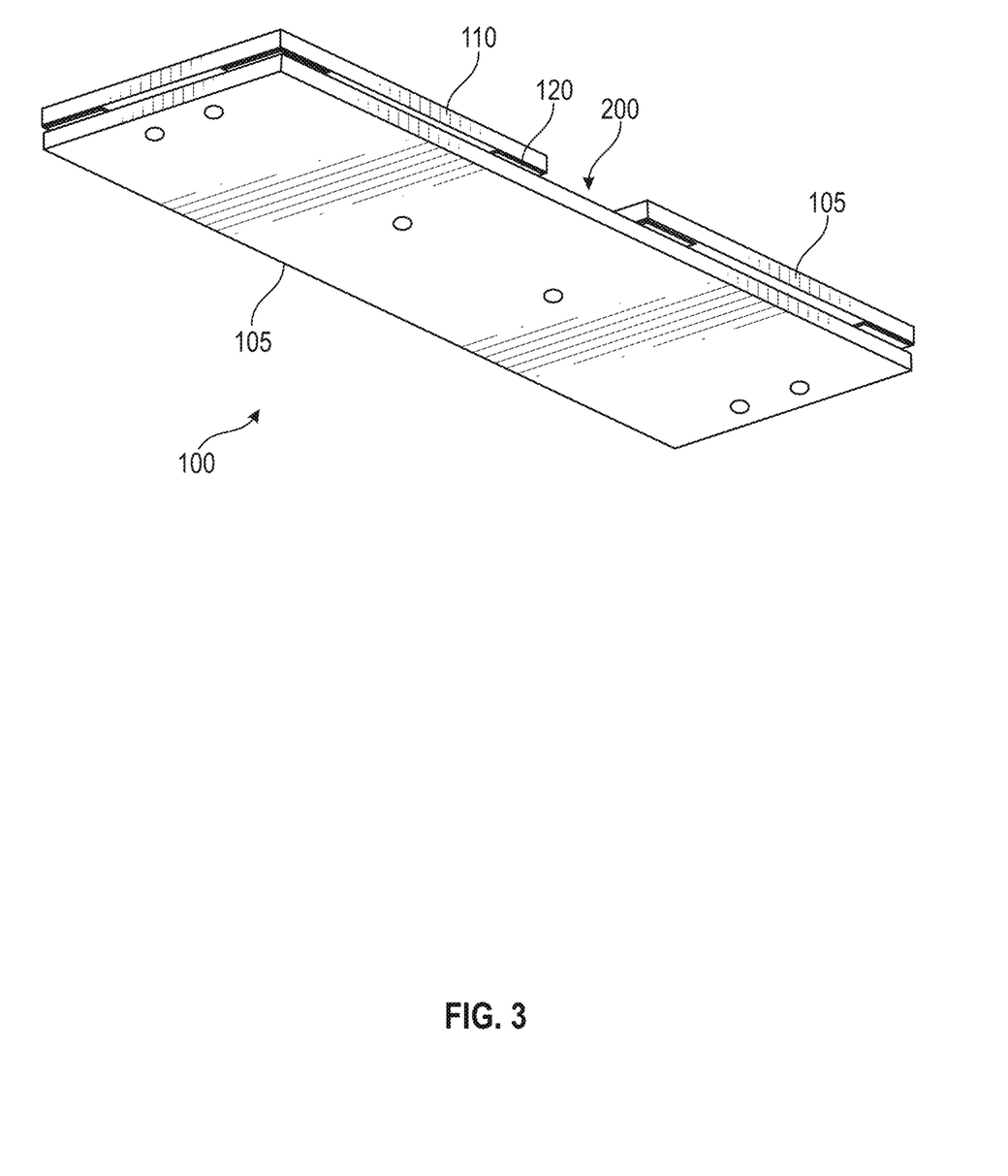
FIG. 3 is a bottom isometric view of an embodiment of the force reading device according to various embodiments of the present disclosure.

In some embodiments, a force measuring device may include a force measuring board 100, as shown in FIGS. 1-3. Specifically, FIG. 1 is an isometric view of an embodiment of the force reading board 100, FIG. 2 is an exploded view of an embodiment of the force reading board 100, and FIG. 3 is a bottom isometric view of an embodiment of the force reading board 100 according to various embodiments of the present disclosure.

The overall dimensions of the force measuring board 100 may include, for instance, 38 inches in length, 12 inches in width, and 1.75 inches in thickness when assembled, although other suitable dimensions can be employed. In some embodiments, the material of the force measuring board 100 is birch plywood that has been machined to allow for bolts, nuts, washers, sensors, spacers, and electronics to be integrated onto the force measuring board 100, although other materials, such as plastic, ceramic, metal, or any combination thereof, may be employed. The force measuring board 100 may include a base 105, a first board plate 110, and a second board plate 115, as well as a recess 120 positioned therebetween. The first board plate 110 and the second board plate 115 of the force measuring board 100 may be secured to the base 105 using nuts and bolts such that the components are secured together without compressing. The first board plate 110 and the second board plate 115 of the force measuring board 100 may be detachable. In some embodiments, they are 16 inches in length by 12 inches in width by ¾ inches in thickness. Centers of sensors 200 may be placed approximately 1.5 inches away from any edge, and may be centered with the first board plate 110 and the second board plate 115 of the force measuring board 100 in some embodiments. In some embodiments, the material of the various components of the force measuring board 100 is a high strength, low elasticity plastic or ceramic.

The force measuring board 100 may include a plurality of sensors 200 configured to measure force. For instance, sensors 200 developed by Chenbo™ can be employed although other suitable sensors may be used. The sensors 200 may include force transducers that react to changes in pressure by changing resistance in an electrical circuit. In the force measuring board 100, four of these sensors 200 may be configured in a wheat-stone bridge on a downward facing side of the force measuring board 100.

Changes in force applied to any of the sensors 200 may produce voltage changes in the 3.3 volt circuit. By configuring the sensors in this regard, a user (e.g., an operator of the force measuring board 100) can stand with most of their weight on any one sensor 200, and the resulting voltage will be similar to as if they were standing with their weight distributed evenly over all four sensors 200. The measuring range for one Chenbo sensor 200 is 50 kg (or 110 lbs), but when the sensors 200 are configured in a full bridge circuit, the measured range for the sensors 200 is 200 kg (or 440 lbs). In some embodiments, a shape of the top of the sensors 200 is rounded, such that the sensors 200 are separated from the top board by a three inch square piece of strengthened acrylic that is about ⅛ inches thick so that the sensors do not dig into the force measuring board 100 and misrepresent the force on the set of sensors 200. The changes in voltage due to the sensors 200 are amplified by an amplifier, such as an Arduino amplifier. The configuration of the sensors 200 may be replicated on the other side of the force measuring board 100 to allow readings for another weight, as may be appreciated.

The processing circuitry of the force measuring board 100 may include its own independent voltage that is also amplified. Both voltage signals then pass from the amplifiers to a microprocessor (e.g., an Adafruit Feather 32u4 Bluefruit LE microprocessor) where the signal is processed to account for anomalies, such as instances when only one side is stepped on, so that anomalies are not represented in data. The processing circuitry may include a microprocessor that uses a wireless protocol (e.g., a Bluetooth low energy 2.4 GHz spectrum wireless protocol) to connect to a computing device, such as a smartphone, personal computer, desktop computer, tablet computer, or other device. In some examples, this microprocessor can employ one of the wireless protocols that you can use with iOS, Android, Windows, or other operating system without requiring a special certification. The readings from the sensors are pushed from this microprocessor to the computing device where they are then processed in a force monitoring application, referred to as a "4rce app" or other suitable application.

Accordingly, the force reading board 100 may include an apparatus comprising a plurality of sensors 200. Each of the plurality of sensors 200 may be configured to measure a force applied to a respective one of the plurality of sensors 200. The force reading board 100 may further include processing circuitry configured to: (a) receive signals from the plurality of sensors 200; (b) determine and display differences in force applied to different portions of the apparatus (e.g., forces applied to the first board plate 110 and the second board plate 115); (c) represent balance of static forces or weights; (c) provide user awareness of forces applied via a mobile application and computing device; (d) display a task on the computing device to improve fitness of the user; and (e) display a task on the computing device to aid in recovery of a muscle group of the user.

Figure 8:
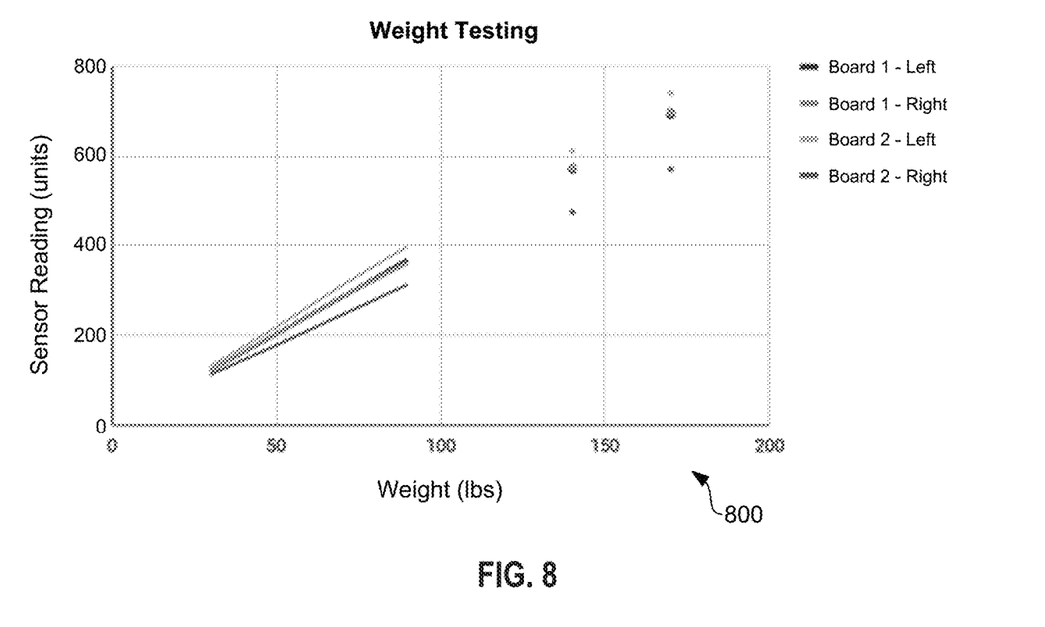
FIG. 8 is calibration data depicting changes in weight that produce readings that align linearly with different weights according to various embodiments of the present disclosure.
Figure 9:
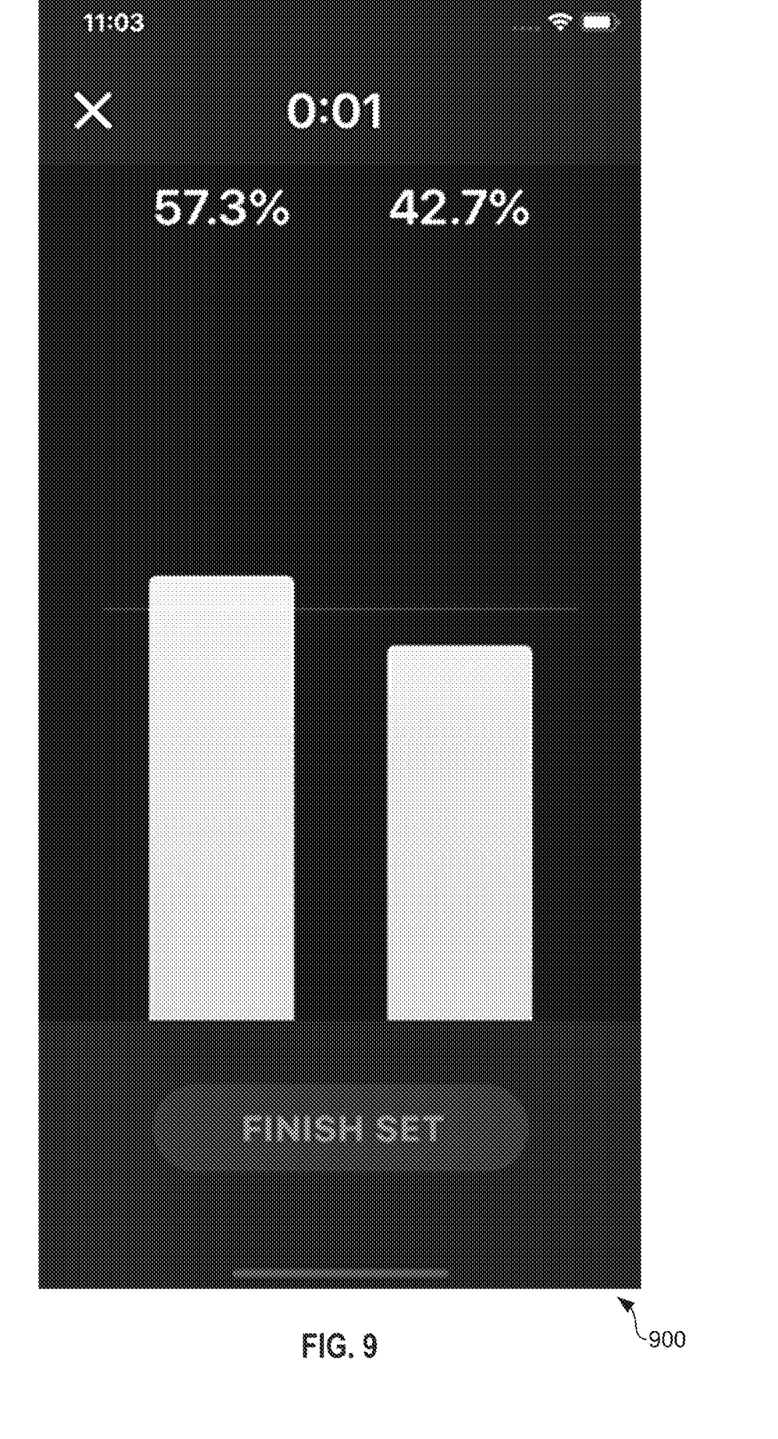
FIG. 9 is a user interface depicting bars indicating how a user's weight is displaced when positioned on the force reading device according to various embodiments of the present disclosure, where 50% on one side represents a user that is balanced.

In the computing device, the received data is configured to reflect changes in balance between the two sides of the force measuring board 100, as shown in FIG. 9. A client application on the computing device can include settings that allow for changes in sensitivity for graphics should change and what color they should change. The client application also allows for calibration of the device. Because the two circuits for each set of sensors 200 are independent, they may not always read the exact same voltage. To accommodate for this, the force measuring board 100 and/or other system can be calibrated using a person's weight. To calibrate, a person may stand on one side of the force measuring board 100, and then switch sides to allow the system to create a ratio for how each set of sensors 200 is operating. This ratio is stored in memory of the computing device by the client application, which can be used for different weights as the resistance in the sensors 200 changes linearly with the amount of force applied, as seen from testing in FIG. 8.

As shown in FIG. 2, a force measuring board 100 for measuring force can include a board base 105, a first board plate 110 positioned on the base 105 for receipt of a first body portion; a second board plate 115 positioned on the base 105 for receipt of a second body portion; and a plurality of sensors 200, where a first portion of the plurality of sensors 200 may be arranged between the first board plate 110 and the board base 105; a second portion of the plurality of sensors 200 are arranged between the second board plate 115 and the board base 105. Processing circuitry of the force measuring board 100 may be configured to analyze signals produced by the plurality of sensors 200 and output a force, for instance, for each of the first body portion and/or the second body portion.

Figure 4:
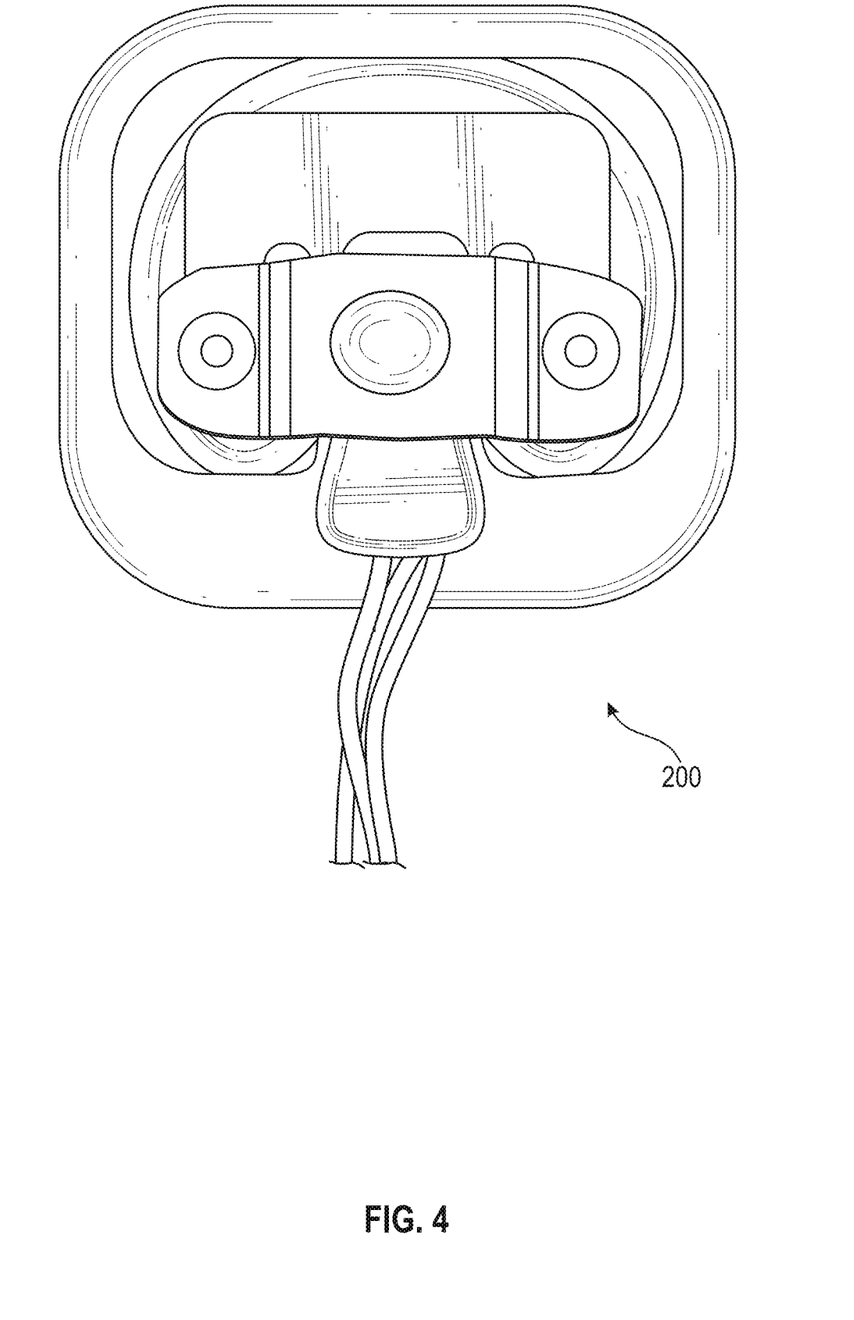
FIG. 4 is a view of an embodiment of a sensor for use in the force reading device according to various embodiments of the present disclosure.

In some embodiments, the force measuring board 100 may be approximately 38 inches in length, 12 inches in width, and each of the first board plate 110 and the second board plate 115 is approximately ¾ inches in thickness (e.g., ±5 inches). A recess 120 may be defined between the first board plate 110 and the second board plate 115, or may be placed directly adjacent to one another. The force measuring board 100 can include a first plurality of spacers positioned between the first board plate 110 and the board base 105, and a second plurality of spacers positioned between the second board plate 115 and the board base 105. In some embodiments, the force measuring board 100 is formed of a strong plastic with adjustable dimensions. FIG. 4 is a view of an embodiment of one of the sensors 200 that may be used in the force reading board 100 according to various embodiments of the present disclosure.

Figure 5:
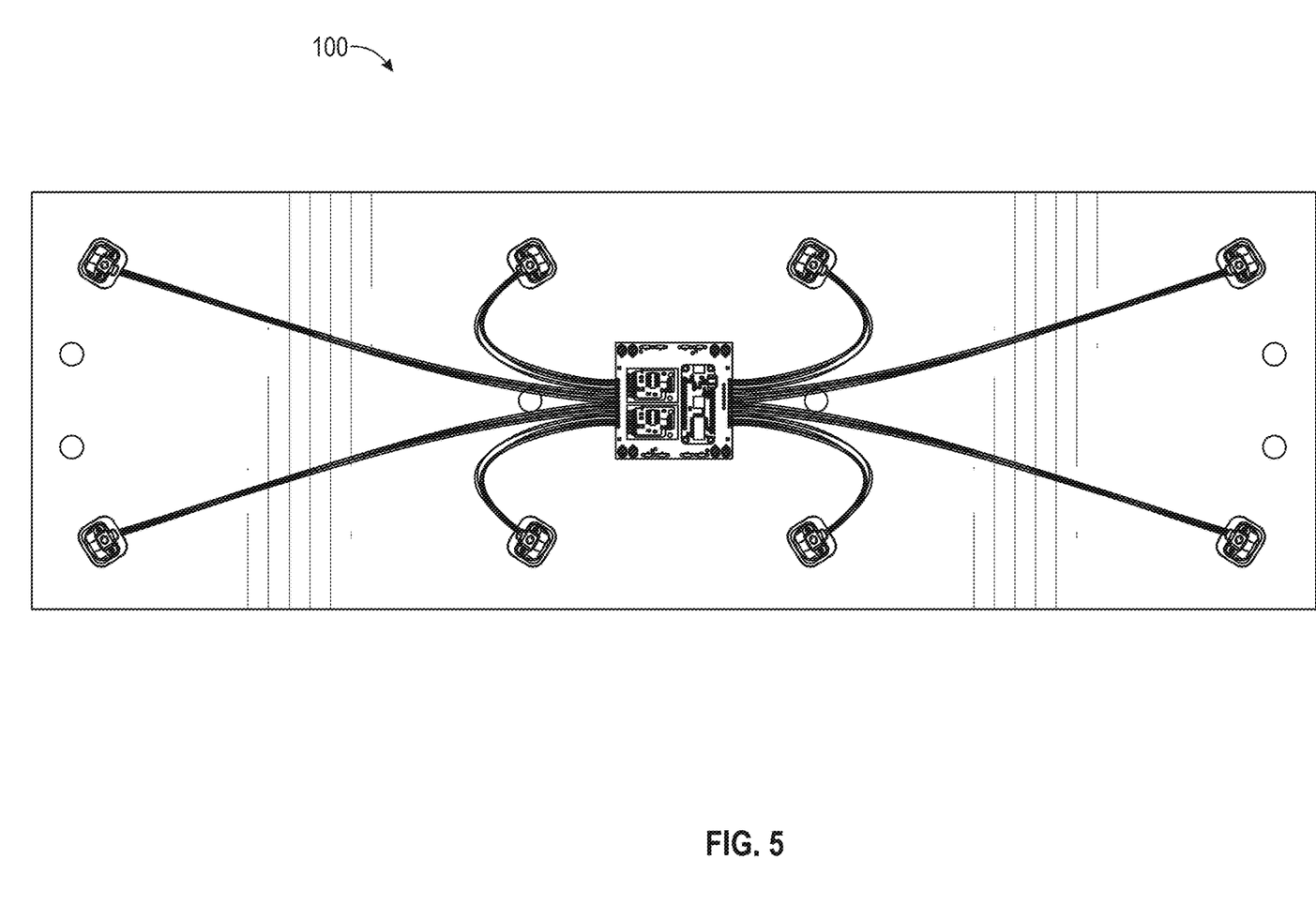
FIG. 5 is an embodiment of a sensor system of the force reading device or other device (e.g., shoe) according to various embodiments of the present disclosure.

FIG. 5 is an embodiment of a sensor system of the force reading board 100 or other device (e.g., shoe) according to various embodiments of the present disclosure. The sensor system may include processing circuitry, which can include at least one microprocessor. As shown in FIG. 5, the first portion of the plurality of sensors 200 can be arranged between the first board plate 110 and the board base 105 in a first wheat-stone bridge arrangement and the second portion of the plurality of sensors 200 can be arranged between the second board plate 115 and the board base 105 in a second wheat-stone bridge arrangement. Table 1 below illustrates data obtained via weight testing of two prototypes. In this test, dumbbells were used to give approximate weights.

TABLE 1

| Weight (lbs) | Board 1 | | Board 2 | |
|---|---|---|---|---|
| | B1 - Left | B1 - Right | B2 - Left | B2 - Right |
| 30 | 120.8 | 121.2 | 130 | 112.1 |
| 50 | 201.8 | 201.8 | 217.2 | 177.2 |
| 70 | 284.4 | 285.5 | 310.5 | 245.2 |
| 90 | 367.1 | 361 | 398 | 312.3 |
| 110 | | | | |
| 130 | | | | |
| 140 | 570.8 | 574.4 | 610.9 | 474.3 |
| 150 | | | | |
| 170 | 692.4 | 697.6 | 739.6 | 571.2 |

Figure 6:
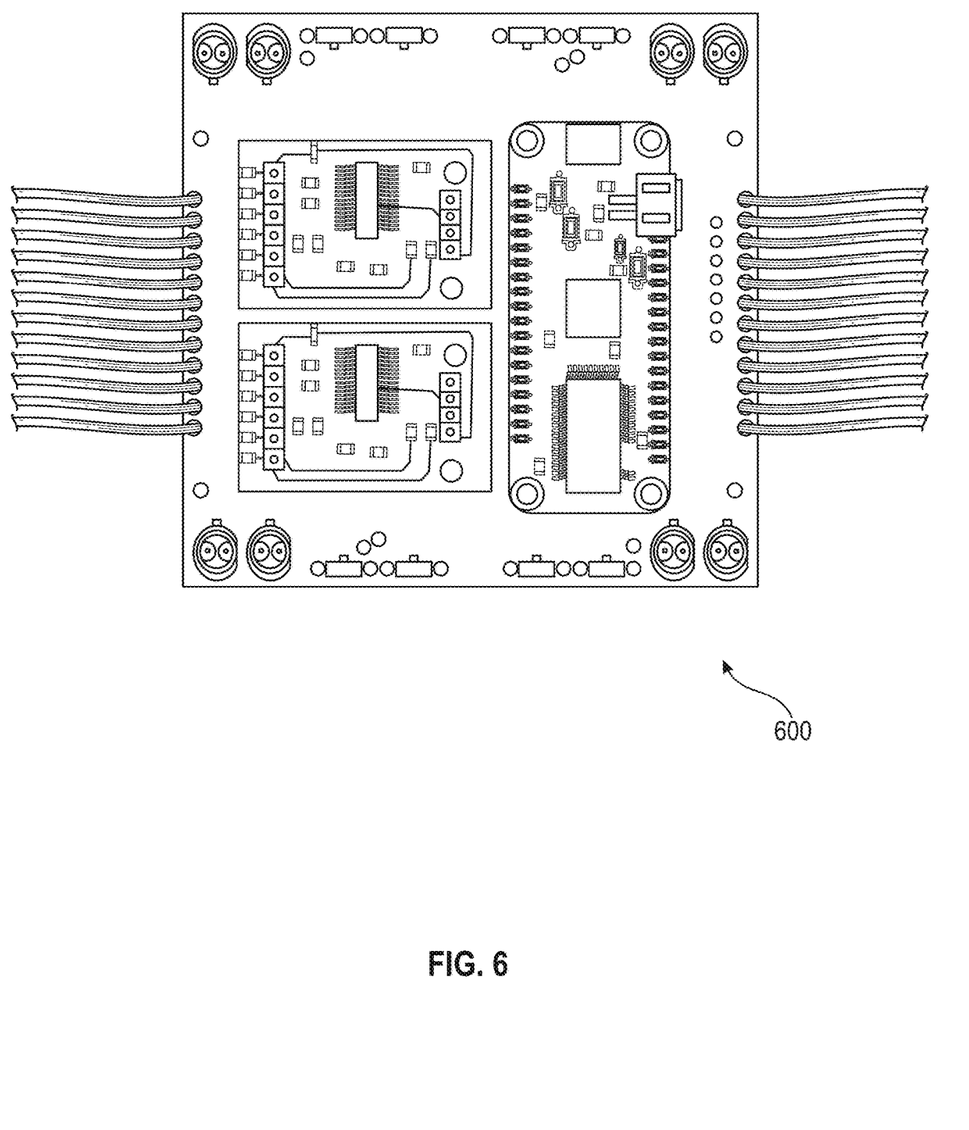
FIG. 6 is an embodiment of an amplifier circuit for use in the force reading device according to various embodiments of the present disclosure.
Figure 7:
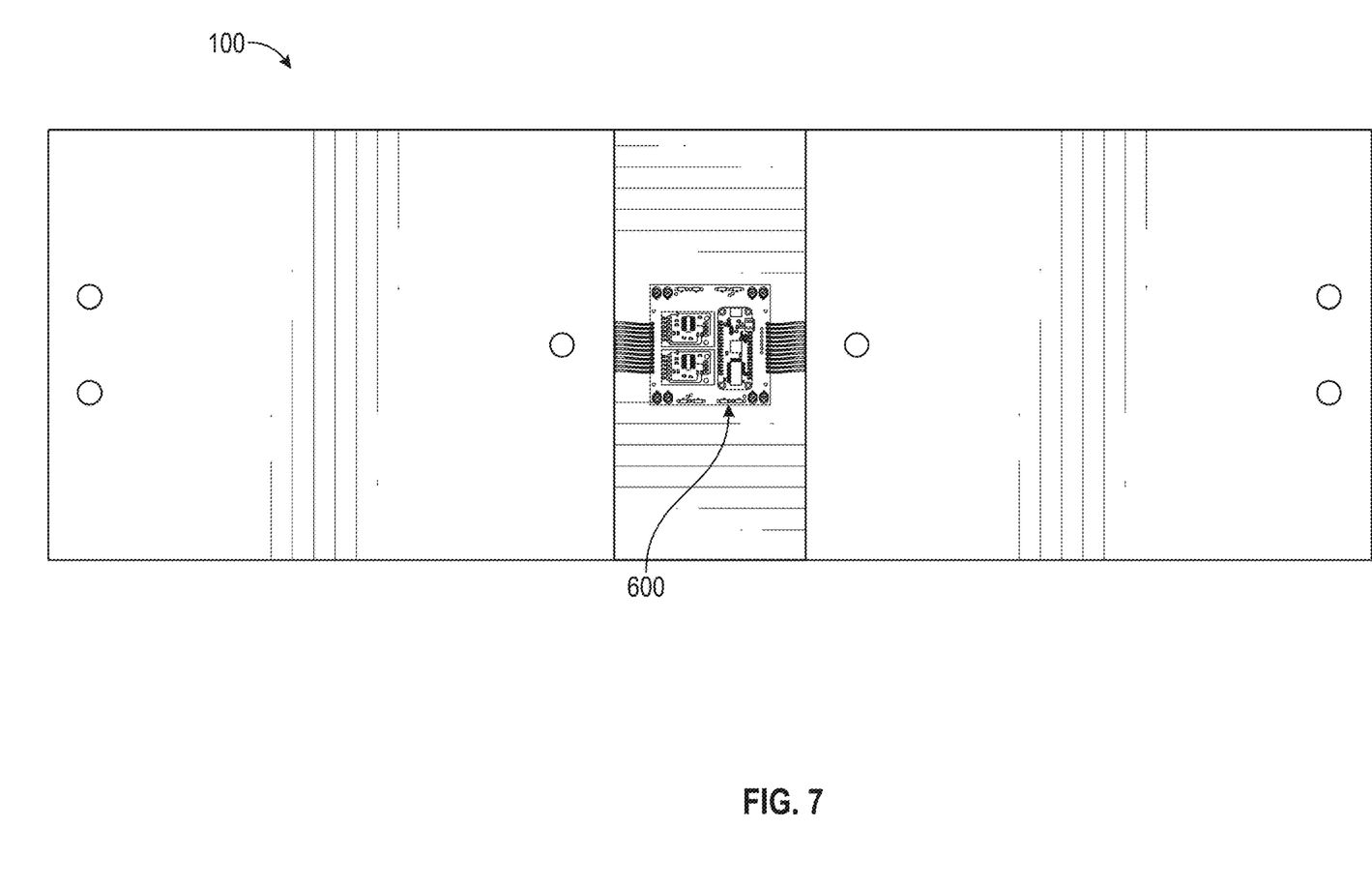
FIG. 7 is a perspective view of an embodiment of the force reading device according to various embodiments of the present disclosure.

FIG. 6 is an embodiment of an amplifier circuit 600 for use in the force reading board 100 according to various embodiments of the present disclosure, and FIG. 7 is a bottom perspective view of an embodiment of the force reading board 100 comprising the amplifier circuit 600 mounted on the base 105 according to various embodiments of the present disclosure.

Figure 10:
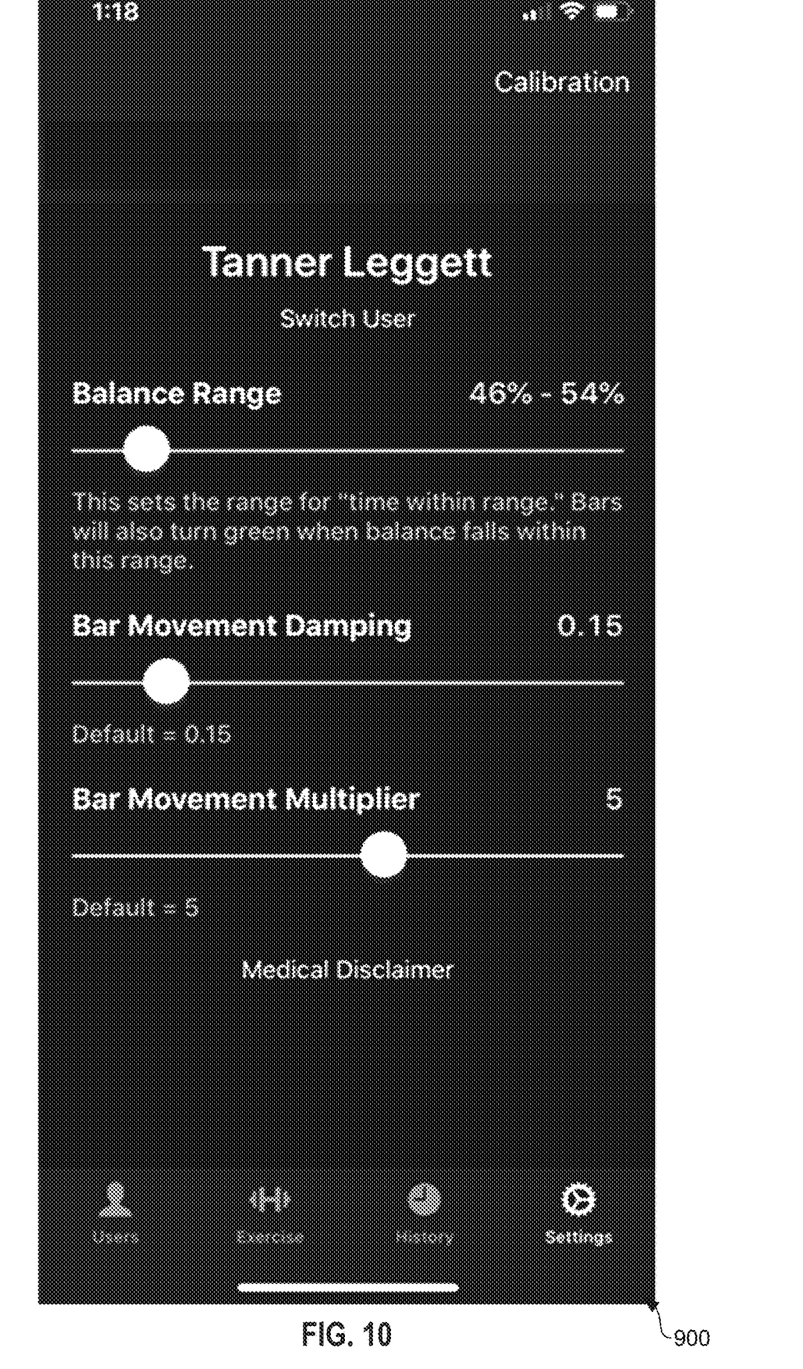
FIG. 10 is an embodiment of a user setting allowing for control over the sensitivity of the bars described in FIG. 9.

FIG. 8 is calibration data includes a chart 800 depicting changes in weight that produce readings that align linearly with different weights according to various embodiments of the present disclosure. FIG. 9 is a user interface 900 depicting bars indicating how a user's weight is displaced when positioned on the force reading device according to various embodiments of the present disclosure, where 50% on one side represents a user that is balanced. FIG. 10 is a user interface 900 showing an embodiment of a user setting allowing for control over the sensitivity of the bars described in FIG. 9. The "Balance Range" may include a range a user would consider 'balanced', the "Bar Movement Dampening" increases or decreases the sensitivity of the sensors, and the "Bar Movement Multiplier" allows the user to adjust what weight range they wish to operate in to receive more accurate results.

Figure 11:
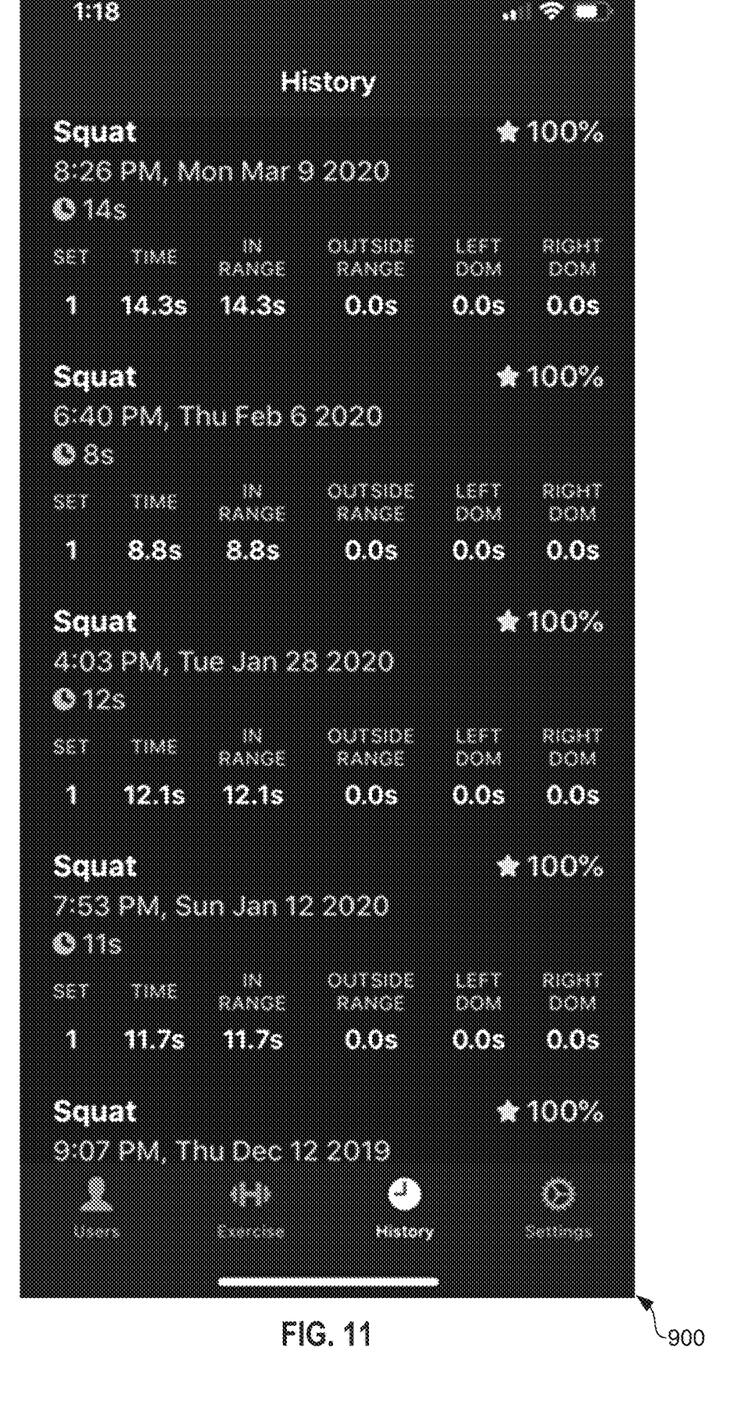
FIG. 11 is a user interface displaying the statistical history of a user's performance such that user results may be tracked over time.
Figure 12:
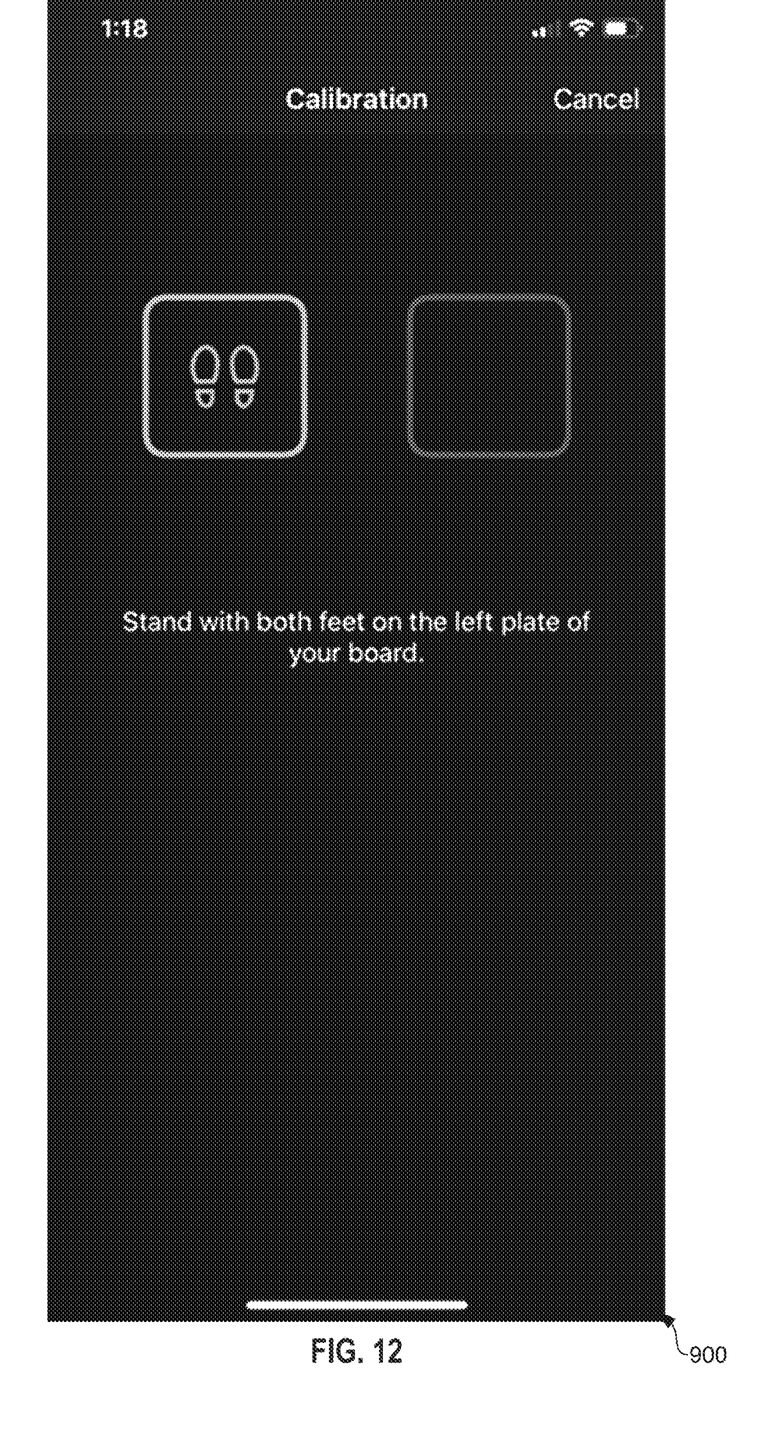
FIG. 12 is a user interface that leads a user through calibrating the device.
Figure 13:
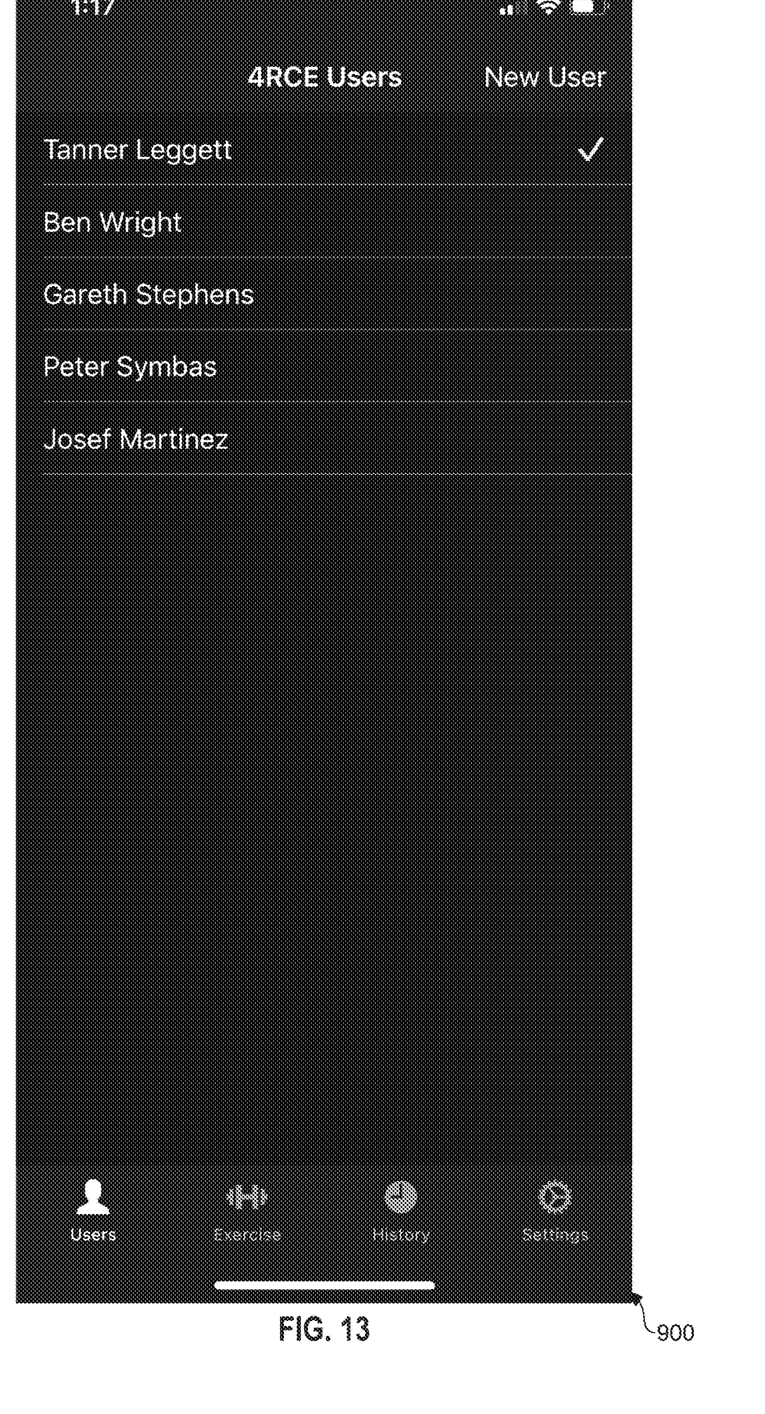
FIG. 13 is a user interface that allows different users to select a specific user profile.
Figure 14:
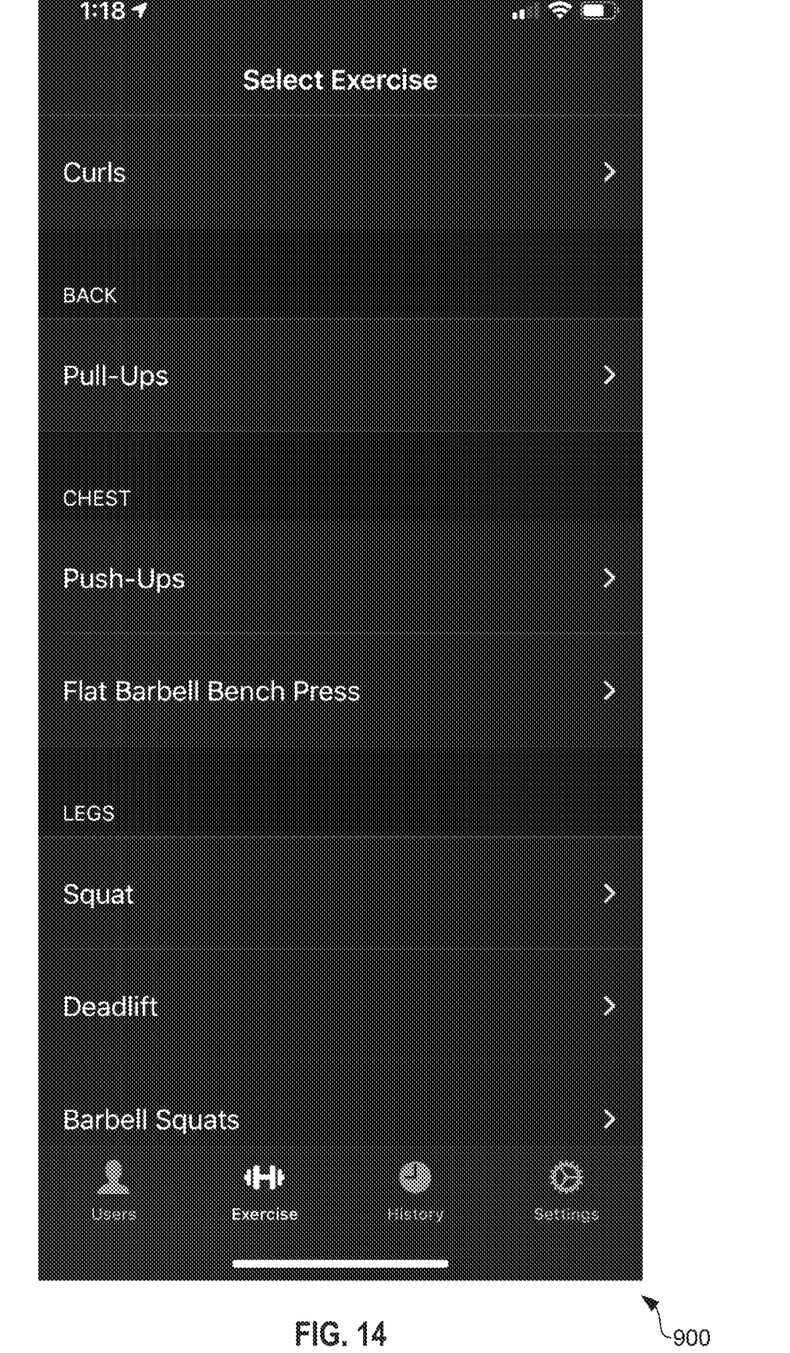
FIG. 14 is an embodiment of a user interface that allows for a user to select a specific exercise, allowing for multiple types of activity to be tracked by the user.

FIG. 11 is a user interface 900 displaying the statistical history of a user's performance such that user results may be tracked over time. FIG. 12 is a user interface 900 that leads a user through calibrating the device. FIG. 13 is a user interface 900 that allows different users to select a specific user profile. FIG. 14 is an embodiment of a user interface 900 that allows for a user to select a specific exercise, allowing for multiple types of activity to be tracked by the user. The user interfaces 900 shown herein may be rendered in a display device, such as a display of a tablet or a smartphone.

Accordingly, an apparatus, system, or electronic device is described that includes a plurality of sensors 200, each of the plurality of sensors 200 being configured to measure a force applied to a respective one of the plurality of sensors 200; and processing circuitry configured to: receive signals from the plurality of sensors 200 to determine and display differences in force applied to different portions of the apparatus; represent balance of static forces or weights through communication with at least one computing device separate from the apparatus; provide user awareness of forces applied through communication with the at least one computing device; display a task to improve fitness of the user through communication with the at least one computing device; and display a task to aid in recovery of a muscle group of the user through communication with the at least one computing device.

In some embodiments, the apparatus may include a force reading board 100 comprising a base 105, a first board plate 110 positioned on a first side of the base, a second board plate 115 positioned on a second side of the base opposite the first side, and the processing circuitry.

The processing circuitry may be configured to provide real time user feedback describing difference in dynamic forces applied to the force reading board through communication with the at least one computing device. In some embodiments, the apparatus may include a communication module configured to use a low energy 2.4 GHz spectrum wireless protocol to connect to the at least one computing device and communicate changes in force using at least one visual aid shown in a user interface of a display device of the at least one computing device.

The processing circuitry may be configured to communicate data representing the difference between forces to the at least one computing device, the at least one computing device being configured to manipulate and store information, the information comprising at least one of: a time and length of an exercise; a number of repetitions performed; a percentage score of overall balance; a time within an accepted and safe range; a time outside an accepted and safe range; and an individual limb score relative to another limb.

The force reading board 100 may further include a plurality of sensors 200, wherein a first portion of the plurality of sensors 200 are arranged between the first board plate 110 and the board base 105; and a second portion of the plurality of sensors 200 are arranged between the second board plate 115 and the board base 105. The dimensions of the force reading board 100 may be approximately 38 inches in length, 12 inches in width, and each of the first board plate 110 and the second board plate 115 being approximately ¾ inches in thickness. A recess 120 may be defined between the first board plate 110 and the second board plate 115. A first plurality of spacers may be positioned between the first board plate 110 and the board base 105, and a second plurality of spacers 200 may be positioned between the second board plate 115 and the board base 105. The processing circuitry comprises at least one microprocessor. The first portion of the plurality of sensors 200 arranged to act in compression when a force is applied are in a first wheat-stone bridge arrangement; and the second portion of the plurality of sensors 200 arranged to act in compression when a force is applied are in a second wheat-stone bridge arrangement.

The computing device can include a processor-based system, such as a computer system, that can include a desktop computer, a laptop computer, a personal digital assistant, a cellular telephone, a smartphone, a set-top box, a music player, a tablet computer system, a game console, an electronic book reader, a virtual reality or augmented reality device, a peripheral device, or any other device with like capability. The client device can also be equipped with networking capability or networking interfaces, including a localized networking or communication capability, such as a near-field communication (NFC) capability, radio-frequency identification (RFID) read or write capability, or other localized communication capability.

The client device can include an operating system, which can be configured to execute various client applications, such as the force measuring application, as well as other applications. Some client applications can access data and other network content served up by a computing environment or other servers, thereby rendering a user interface on a display, such as a liquid crystal display (LCD), touchscreen display, or other type of display device. To this end, some client applications can include a browser or a dedicated application, and a user interface can include a network page, an application screen, or other interface.

The computing devices or devices included in a computing environment can include at least one processor circuit, for example, having a processor and at least one memory device, both of which are coupled to a local interface, respectively. The device can include, for example, at least one computer, a mobile device, smartphone, computing device, or like device. The local interface can include, for example, a data bus with an accompanying address/control bus or other bus structure.

Stored in the memory device are both data and several components that are executable by the processor. In particular, stored in the one or more memory devices and executable by the device processor can be the client application and potentially other applications. Also stored in the memory can be a data store and other data.

A number of software components are stored in the memory and executable by a processor. In this respect, the term "executable" means a program file that is in a form that can ultimately be run by the processor. Examples of executable programs can be, for example, a compiled program that can be translated into machine code in a format that can be loaded into a random access portion of one or more of the memory devices and run by the processor, code that can be expressed in a format such as object code that is capable of being loaded into a random access portion of the one or more memory devices and executed by the processor, or code that can be interpreted by another executable program to generate instructions in a random access portion of the memory devices to be executed by the processor. An executable program can be stored in any portion or component of the memory devices including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

Memory can include both volatile and nonvolatile memory and data storage components. Also, a processor can represent multiple processors and/or multiple processor cores, and the one or more memory devices can represent multiple memories that operate in parallel processing circuits, respectively. Memory devices can also represent a combination of various types of storage devices, such as RAM, mass storage devices, flash memory, or hard disk storage. In such a case, a local interface can be an appropriate network that facilitates communication between any two of the multiple processors or between any processor and any of the memory devices. The local interface can include additional systems designed to coordinate this communication, including, for example, performing load balancing. The processor can be of electrical or of some other available construction.

The computing devices can include a display upon which a user interface generated by the client application or another application can be rendered. In some examples, the user interface can be generated using user interface data provided by a computing environment, which can include a server. The computing device can also include one or more input/output devices that can include, for example, a capacitive touchscreen or other type of touch input device, fingerprint reader, or keyboard.

Although various systems described herein can be embodied in software or code executed by general-purpose hardware as discussed above, as an alternative, the same can also be embodied in dedicated hardware or a combination of software/general-purpose hardware and dedicated hardware. If embodied in dedicated hardware, each can be implemented as a circuit or state machine that employs any one of or a combination of a number of technologies. These technologies can include discrete logic circuits having logic gates for implementing various logic functions upon an application of one or more data signals, application specific integrated circuits (ASICs) having appropriate logic gates, field-programmable gate arrays (FPGAs), or other components.

Also, any logic or application described herein that includes software or code can be embodied in any non-transitory computer-readable medium for use by or in connection with an instruction execution system such as, for example, a processor in a computer system or other system. In this sense, the logic can include, for example, statements including program instructions, program code, and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can include any one of many physical media, such as magnetic, optical, or semiconductor media. More specific examples of a suitable computer-readable medium include solid-state drives or flash memory. Further, any logic or application described herein can be implemented and structured in a variety of ways. For example, one or more applications can be implemented as modules or components of a single application. Further, one or more applications described herein can be executed in shared or separate computing devices or a combination thereof. For example, a plurality of the applications described herein can execute in the same computing device, or in multiple computing devices.

It is emphasized that the above-described examples of the present disclosure are merely possible examples of implementations set forth for a clear understanding of the principles of the disclosure. Many variations and modifications can be made to the above-described examples and embodiments without departing substantially from the spirit and Therefore, the following is claimed:

1. An apparatus, comprising:
a base, a first board plate positioned on a first side of the base, a second board plate positioned on a second side of the base opposite the first side;
a plurality of sensors, each of the plurality of sensors being configured to measure a force applied to a respective one of the plurality of sensors;
a first circuit comprising a first portion of the plurality of sensors positioned between the first board plate and the base, the first circuit generating a first voltage;
a second circuit comprising a second portion of the plurality of sensors positioned between the second board plate and the base, the second circuit generating a second voltage;
processing circuitry configured to:
receive the first voltage from the first circuit and the second voltage from the second voltage to determine and display differences in force applied to different portions of the apparatus based at least in part on a predetermined ratio of the first circuit to the second circuit, the predetermined ratio being stored in memory in association with a predetermined weight;
represent balance of static forces or weights through communication with at least one computing device separate from the apparatus;
provide user awareness of forces applied through communication with the at least one computing device;
display a task to improve fitness of the user through communication with the at least one computing device; and
display a task to aid in recovery of a muscle group of the user through communication with the at least one computing device.

2. The apparatus of claim 1, wherein the apparatus is a force reading board.

3. The apparatus of claim 2, wherein the processing circuitry is further configured to provide real time user feedback describing difference in dynamic forces applied to the force reading board through communication with the at least one computing device.

4. The apparatus of claim 3, further comprising a communication module configured to use a low energy 2.4 GHz spectrum wireless protocol to connect to the at least one computing device and communicate changes in force using at least one visual aid shown in a user interface of a display device of the at least one computing device.

5. The apparatus of claim 4, wherein the processing circuitry is further configured to communicate data representing the difference between forces to the at least one computing device, the at least one computing device being configured to manipulate and store information, the information comprising at least one of: a time and length of an exercise; a number of repetitions performed; a percentage score of overall balance; a time within an accepted and safe range; a time outside an accepted and safe range; and an individual limb score relative to another limb.

6. The apparatus of claim 2, wherein a first portion of the plurality of sensors are arranged between the first board plate and the board base; and a second portion of the plurality of sensors are arranged between the second board plate and the board base.

7. The apparatus of claim 6, wherein dimensions of the force reading board are approximately 38 inches in length, 12 inches in width, and each of the first board plate and the second board plate being approximately ¾ inches in thickness.

8. The apparatus of claim 7, wherein a recess is defined between the first board plate and the second board plate.

9. The apparatus of claim 8, further comprising a first plurality of spacers positioned between the first board plate and the board base, and a second plurality of spacers positioned between the second board plate and the board base.

10. The apparatus of claim 6, wherein:
the first portion of the plurality of sensors are four sensors arranged to act in compression when a force is applied are in a first wheat-stone bridge arrangement, wherein the four sensors thereof are positioned at respective corners of the first board plate; and
the second portion of the plurality of sensors are four sensors arranged to act in compression when a force is applied are in a second wheat-stone bridge arrangement, wherein the four sensors thereof are positioned at respective corners of the second board plate.

11. The apparatus of claim 1, wherein the processing circuitry comprises at least one microprocessor.

12. The apparatus of claim 1, wherein at least one of the first circuit and the second circuit generate a predetermined voltage that is a positive integer, wherein the force applied to the different portions of the apparatus cause a measurable voltage change in the predetermined voltage.

13. The apparatus of claim 12, wherein the predetermined voltage is 3.3 V.

14. The apparatus of claim 12, wherein the predetermined ratio is determined in response to a calibration of the first portion of the plurality of sensors and the second portion of the plurality of sensors.

* * * * *